United States Patent [19]

Hughes

[11] 4,326,409
[45] Apr. 27, 1982

[54] SITU BORE HOLE TEST PROBE

[76] Inventor: John M. O. Hughes, 533 East 5th, North Vancouver, British Columbia, Canada

[21] Appl. No.: 151,139

[22] Filed: May 19, 1980

[51] Int. Cl.³ .............................................. G01N 3/00
[52] U.S. Cl. .......................................................... 73/84
[58] Field of Search ................... 73/151, 784, 84, 818, 73/825

[56] References Cited

U.S. PATENT DOCUMENTS 3,442,123  5/1969  Broise ..................................... 73/151
3,499,320  3/1970  Fox et al. ........................... 73/151 X Primary Examiner—Jerry W. Myracle
Attorney, Agent, or Firm—Seed, Berry, Vernon & Baynham

[57] ABSTRACT

A probe for measuring the characteristics of soil, rock and the like surrounding a bore hole. The probe includes a hollow cylindrical body surrounded by a resilient membrane. The ends of the membrane are clamped to the cylindrical body, and a pressurized fluid is injected into the cylindrical body to expand the membrane until it contacts the walls of the bore hole. Feeler members which are resiliently biased in a radially outward direction contact a relatively large area of the membrane so that the outward movements of the feeler members are a function of the outward expansion of the membrane. The feeler members are instrumented with strain gauges to measure the expansion of the membrane which, along with measurements of the fluid pressure producing the expansion, provides an indication of the stiffness and strength of the material surrounding the bore hole. Reinforcing fingers surrounding the membrane near its junction with the body reinforce the membrane against relatively strong shear forces existing at the junction.

11 Claims, 5 Drawing Figures

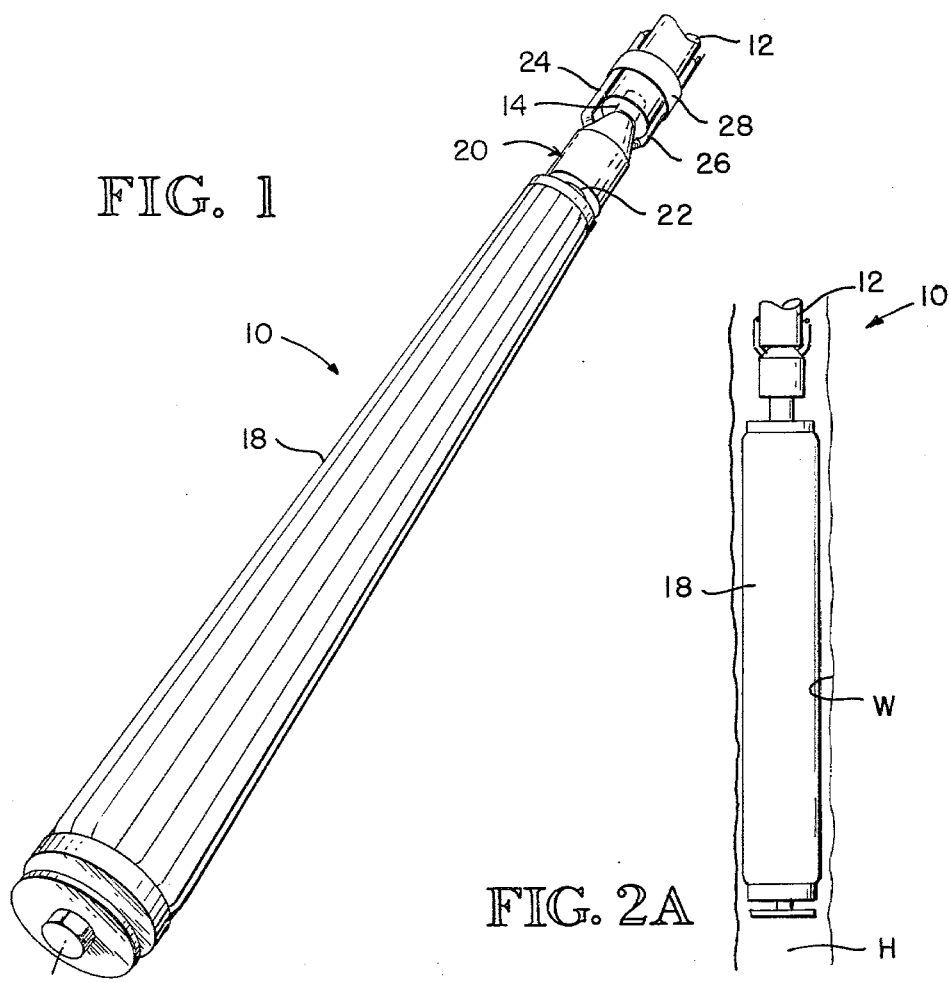
FIG. 1
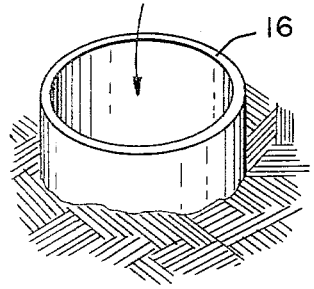
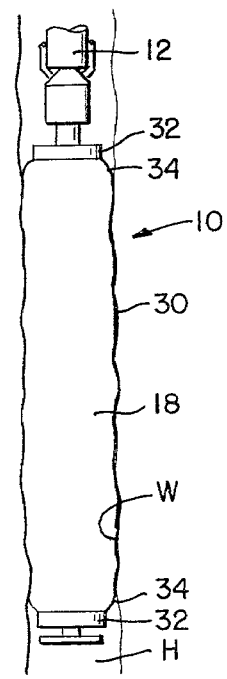
FIG. 2A
FIG. 2B

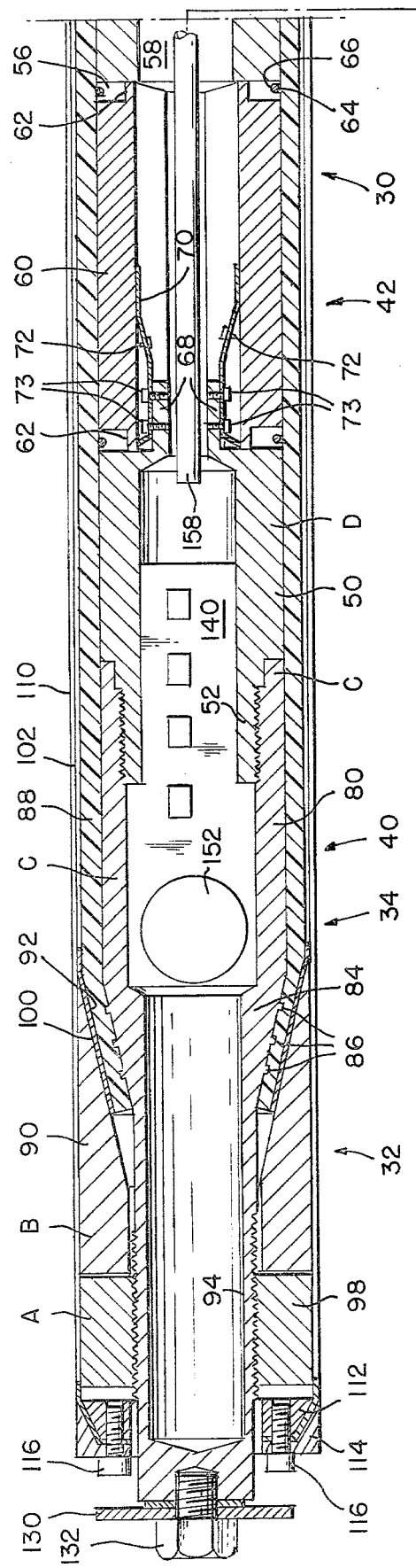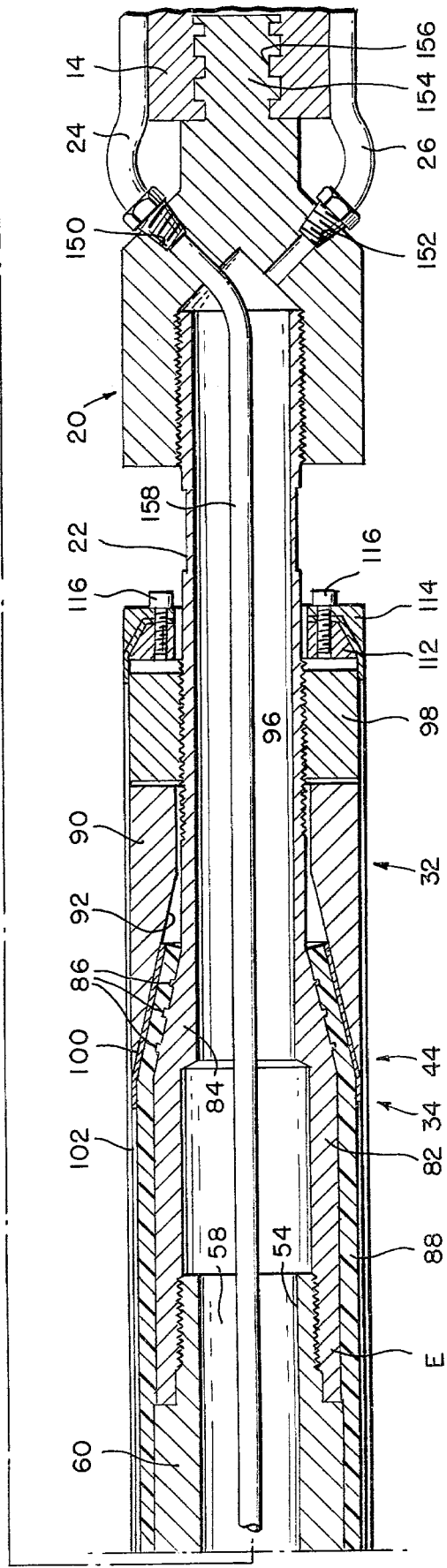

SITU BORE HOLE TEST PROBE

BACKGROUND OF THE INVENTION

1. Field of the Invention

This invention relates to a device for testing the characteristics of material surrounding a bore hole, and more particularly to a bore hole test probe utilizing an expansion membrance which is pressurized to contact the walls of the bore hole.

2. Description of the Prior Art

It is important in a variety of fields to determine characteristics of soil, rocks and the like at various levels beneath the surface of the ground. For example, it is important to note the properties of a site on which a building is to be constructed in order to properly design for settling of the building.

One technique for measuring soil properties at various levels is described in British Pat. No. 1,430,239 issued to National Research Development Corporation. The National Research device is commercially available and in common use, and it is known as a "camkometer" probe. Basically, the camkometer is a probe which is inserted into a usually vertical bore hole to determine the properties of the material surrounding the bore hole. The camkometer includes a cylindrical body surrounded by a resilient expansion membrane. The body, which is secured to the lower end of a pipe extending into the bore hole, has a hollow core which communicates with the interior of the pipe. The probe also includes pivotally mounted feeler members contacting the inner surface of the expansion membrane along a line to measure its expansion. In use, pressure is applied to the pipe from above, causing the expansion membrane to expand against the wall of the bore hole. At the same time, the expansion of the membrane is measured by the feeler members, and this expansion in relation to the pressure applied to the pipe provides an indication of the properties of the material surrounding the bore hole.

Although the above-described bore hole test probe is satisfactory for most uses, it is nevertheless limited in both its accuracy and the pressure which may be applied to the expansion membrane. When the expansion membrane contacts the wall of the bore hole, the pressure differential, and hence the shear stress across the membrane, approaches zero since the outwardly directed force of the fluid pressure is equalized by the inwardly directed force of the wall of the bore hole. However, the ends of the expansion membrane extending between the probe and the wall of the bore hole are subject to substantial shear forces, because this area of the expansion membrane does not contact the wall of the bore hole and thus there is; nothing to generate a force opposing the force produced by the fluid pressure. Consequently, the expansion membrane has a tendency to rupture near its junction with the body. To avoid rupture, the pressure applied to the expansion member must be limited to a relatively low value. Yet, some soil conditions require a relatively high pressure to be applied to the test probe.

Another limitation in the accuracy of the abovedescribed bore hole probe stems from a lack of uniformity in the expansion of the membrane resulting from the nonhomogeneity of the material surrounding the bore hole. The feeler members in the conventionally used bore hole test probe contact the inner surface of the expansion membrane along a relatively small area. Yet the expansion of the membrane in the area may differ significantly from the average expansion of the membrane in the vicinity of the feeler members, and it is the average expansion which is most indicative of the properties of the material surrounding the bore hole.

Both of the aforementioned limitations of the conventionally used bore hole test probe (1) reduce the accuracy of measurements, and (2) limit pressures to be applied to the expansion membrane.

SUMMARY OF THE INVENTION

It is an object of the invention to provide a bore hole test probe of the type utilizing a resilient expansion membrane which is able to withstand substantially higher pressures than heretofore possible.

It is another object of the invention to provide a bore hole test probe of the type utilizing a resilient expansion membrane which provides an indication of membrane expansion indicative of the average property of the material surrounding the bore hole over a fairly large area.

It is still another object of the invention to provide an improved bore hole test probe which is capable of utilizing the techniques and equipment of conventionally used bore hole test probes.

These and other objects of the invention are provided by a bore hole test probe having a cylindrical body with a hollow core. A resilient cylindrical expansion membrane surrounds the body and a fluid passage extends between the core and the expansion member so that fluid pressure applied through the core expands the expansion membrane. The ends of the expansion membrane extend into the body and are clamped thereto.

A feeler mechanism is resiliently biased against the inside surface of the expansion member to provide an indication of the radial expansion of the membrane responsive to pressure applied to the core of the body. The feeler members preferably contact the inner surface of the expansion membrane over a relatively large area so that the radial movement of the feeler members is proportional to the average expansion of the membrane over a fairly wide area. The feeler members thus provide an indication of the average properties of the material surrounding the bore hole instead of an indication of its properties at a single point.

The feeler members are preferably resiliently biased in a radially outward direction by a resilient spring which carries a strain gauge to provide an electrical indication of the radial movement of the feeler members and hence the radial expansion of the membrane. The feeler members are preferably biased at a point intermediate their ends so that they can rotate about that point to flushly contact the inside surface of the membrane.

Reinforcing fingers preferably extend from the body along the outer surface of the expansion membrane to reinforce the expansion membrane against relatively strong shear stresses produced in this area. The reinforcing fingers provide an inwardly directed force partially counteracting the outwardly directed force of the fluid pressure to allow relatively high fluid pressures to be applied to the probe.

BRIEF DESCRIPTION OF THE DRAWINGS

FIG. 1 is an isometric view of the test probe being lowered into a bore hole;

FIGS. 2A and 2B are schematics showing the test probe within a bore hole in its nonexpanded and expanded conditions, respectively;

FIG. 4 is a cross-sectional view of the bore hole test probe.

DETAILED DESCRIPTION OF THE INVENTION

Figure 3:
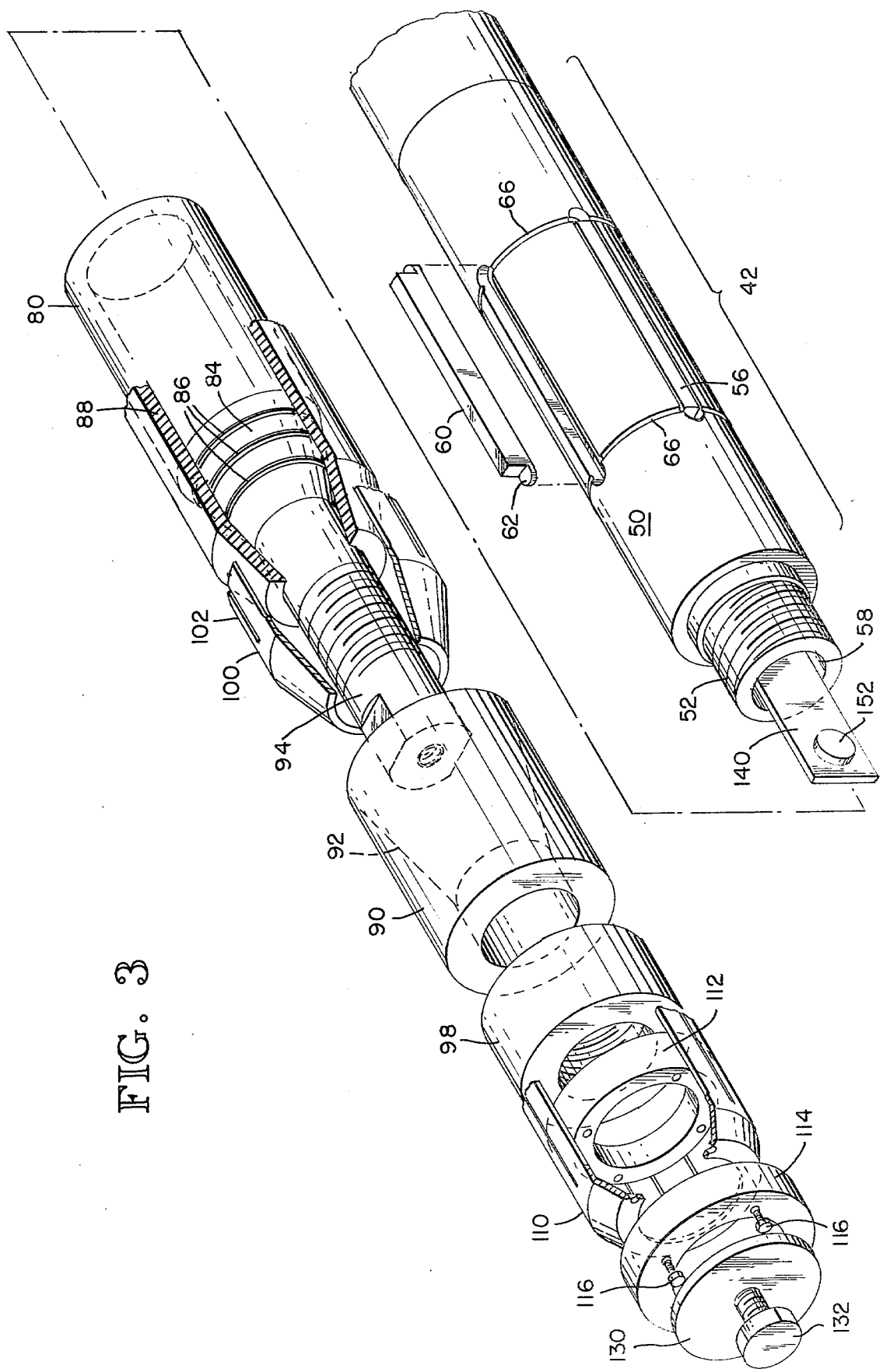
FIG. 3 is an exploded isometric view of the bore hole test probe partially broken away to show internal structure.

A bore hole test probe is illustrated in use in FIG. 1. The probe 10 is mounted on the lower end of a drill stem 12 through a conventional fitting 14 formed at the upper end of the probe 10. The probe 10 is lowered into a bored hole, the upper end of which is surrounded by a casing 16. The probe 10 includes a selectively expandable portion 18 connected to an attachment portion 20 by a cylindrical pipe 22. A pair of hoses 24, 26 connected to respective ports formed in the interconnecting portion 20 extend along the drill stem 12 and are secured thereto by bands 28. The hoses 24, 26 allow fluid communication between the interior of the probe 10 and a conventional surface control unit as well as providing passage for electrical measurement leads extending from the probe 10 to a conventional readout device.

A schematic illustrating the operation of the test probe is illustrated in FIG. 2A. The probe 10 is lowered into a bore hole H, the walls W of which are slightly larger than the diameter of the expandable portion 18 so that the probe 10 can easily be inserted into the hole H. When the probe 10 has been lowered to the proper depth, pressurized fluid is pumped into the probe 10 thereby causing the expandable portion 18 to expand against the walls W of the bore hole H, all illustrated in FIG. 2B. As explained in greater detail hereinafter, the walls of the expandable portion 18 are formed by a resilient membrane. The pressure on opposite sides of the membrane at the center of the expandable portion 18, generally designated as 30, is zero since the pressure exerted on the inside surface of the membrane by the hydraulic fluid is equal to the inwardly directed pressure exerted on the outer surface of the membrane by the wall W of the bore hole H. The end portions of the membrane, generally indicated at 32, are clamped so that the pressure of the fluid on the inside wall of the membrane in this area is resisted by relatively strong clamps. However, there are no surrounding structures to resist the outwardly directed forces on the membrane in the area between the center 30 and the ends 32, generally designated at 34. In other words, the outward forces of the bladder caused by the pressurized fluid is resisted by the wall W of the bore hole H at 30 and by relatively strong clamps at 32, but there are no structures to resist outwardly directed forces in the area 34. Consequently, the membrane is subject to fairly high shear stresses at the portion 34, which limit the pressure which may be applied to the probe 10.

As also illustrated in FIG. 2B, the wall W of the bore hole H is generally not uniform since the material surrounding the bore hole H is generally not homogeneous. Consequently, the wall W is somewhat wavy or irregular. Measuring the outward movement of the expanding portion 18 at a single point or line along the wall W is likely to produce errors, since the measurement is based upon the characteristics of only a small portion of the wall W. However, the expansion of the inventive bore hole test probe is measured over a relatively large area of the wall W so that the average property of the material surrounding the bore hole is measured. This technique thus markedly increases the accuracy of measurements taken with the inventive test probe as compared with conventional test probes which measure the expansion along a point or line.

The structural details of the bore hole test probe are illustrated in FIGS. 3 and 4. The expandable portion 18 includes three basic sections, namely, a lower end section 40, a midsection 42 and an upper end section 44. The center section 42 includes a cylindrical body 50 having a threaded flange 52, 54 at each end. A plurality of circumferentially spaced longitudinal slots 56 are formed in the body 50 which allow communication with a center cavity 58. An elongated feeler member 60 is loosely received in each of the slots 56 so that the feeler members 60 can move radially within their respective slots 56. A retaining tab 62 is formed at the ends of each feeler member 60 toward the center of the body 50. Annular rings 64 positioned in grooves 66 extending around the circumference of the body 50 contacts the retaining tabs 62 to prevent the feeler members 60 from being pushed out of the slots 56.

A mounting plate 68 is integrally formed with the body 50 adjacent each slot 56. A spring 70 secured to each of the mounting plates 68 by bolts 73 contacts the inside surface of its respective feeler member 60 to resiliently bias the feeler members 60 in a radially outward direction. Respective strain gauges 72 mounted on the springs 70 provide an electrical indication of the deflection of the springs 70 and hence the radial movement of the feeler members 60. The springs 70 are thus provided solely for the purpose of measuring radial movement of the feeler members 60 and not for applying appreciable outwardly directed forces to the feeler members 60. Instead, the feeler members 60 are permitted to move outwardly by movement of an expansion membrane as hydraulic fluid is applied to the cavity 58 as explained hereinafter.

The end portions 40, 44 are somewhat similar to each other in structure and function. The end sections 40, 44 also include respectively cylindrical bodies 80, 82 which are threaded onto the threaded flanges 52, 54, respectively, of the body 50. The bodies 80, 82 each include a tapered portion 84 having a plurality of axially spaced, circumferential grooves 86 formed along their outer surface. A resilient expansion membrane 88 of generally cylindrical configuration extends from the tapered portion 84 of one body 80 to the tapered portion 84 of the other body 82 and thus completely surrounds the center section 42. Respective clamp members 90 each having an internal surface 92 tapered to match the taper of the tapered portions 84 slips over reduced diameter portions 94, 96 of the bodies 80, 82, respectively. The clamps 90 are forced toward each other by respective collars 98 which are threaded onto the reduced diameter portions 94, 96 of respective bodies 80, 82. The clamps 90 thus compress the ends of the expansion membrane 88 against the grooves 86 and the tapered portions 82, 84. The grooves 86 morer securely hold the ends of the bladder 88 in place and provide more effective sealing of hydraulic fluid within the cavity 58.

As explained above in reference to FIG. 2B, the outward force exerted on the expansion membrane 88 is resisted by the wall W of the bore hole H in the center area 30. The outward force on the expansion membrane 88 at its end 34 is resisted by the clamps 90. However, no structure has heretofore been used to resist the outward force exerted on the expansion membrane 88 in the midportions 34 between the center area 30 and the ends 32 which do not contact the walls of the bore hole. In accordance with the invention, a reinforcing collar 100 having a plurality of reinforcing fingers 102 projecting therefrom is positioned between each of the clamps 90 and the membrane 88. The reinforcing fingers 102 exert sufficient inward force on the expansion membrane 88 to resist excessive shear forces imparted to the membrane 88 and thus allow the use of significantly higher fluid pressures in the cavity 58.

It is also important to note with respect to FIG. 2B that the expansion membrane 88 will conform to the shape of the wall W of the bore hole H and that the feeler members 60 contact the inside surface of the membrane 88 over a fairly large area. Thus the feeler members 60 do not measure a point or line expansion of the membrane 88, and hence the bore hole but instead measure the expansion of the membrane 88, and hence bore hole H, over a relatively wide area.

As the probe 10 is lowered into a borehole, the exterior of the probe 10 is subject to much abrasion which would quickly deteriorate the expansion membrane 88. Consequently, a plurality of flexible strips 110, preferably of stainless steel, extend longitudinally along the outside of the membrane 88. The ends of the strips 110 are clamped between a first collar 112 fitting around the reduced diameter portions 94, 96 and respective second collars 114 which are secured to their respective first collars 112 by bolts 116. The bolts are torqued to compress the ends of the protective strips 110 between the collars 112, 114 to retain the protective strips 110 in place. The retaining collars 112, 114 are free to axially slide along the reduced diameter portions 94, 96 of respective end bodies 80, 82, but the strips 110 prevent the collars 112, 114 from moving axially with respect to each other. However, a retaining disc 130 is secured to the end of the body 80 of the lower end section 40 by a bolt 132 to retain the collars 112, 114 in place if the collars 112, 114 are wedged against a rock as the probe 10 is being pulled from the bore hole.

A circuit board 140 containing conventional electronic circuits is positioned in the cavity 58. The circuit board 140 contains conventional amplifiers and other strain gauges (not shown) arranged in a wheatstone bridge for providing an electrical signal proportional to the deflection of the springs 70 while also compensating for temperature effects. The circuit board 140 also contains a conventional pressure cell 152 which provides an electrical signal indicative of the pressure within the cavity 58. Wires from the circuit board 140 extend through the cavity 58 and into one of the hoses 24, 26 (FIG. 1) to a conventional readout device (not shown).

The attachment portion 20 is threaded onto the pipe 22 integrally formed by the body 82 of the upper section 44. The attachment portion contains a pair of fluid ports 150, 152 and has an integrally formed stub 154 in which threads 156 are formed. As explained above in reference to FIG. 1, a conventional fitting 14 of a drill stem 12 is threaded onto the stub 154 to secure the probe 10 to the drill stem 12. Hoses 24, 26 are threaded into the fluid ports 150, 152 to provide fluid communication between the cavity 58 and a conventional surface control unit. A tube 158 communcating with one of the fluid ports 150 extends along the cavity 58 to a point just above the circuit board 140. The tube 158 allows hydraulic fluid to be pumped from the cavity 58 by injecting air through the port 152, thereby forcing hydraulic fluid up the tube 158 and out the port 150. It is generally necessary to remove hydraulic fluid from the cavity 58 when the probe 10 is removed from a dry hole, or else the weight of the hydraulic fluid forces the expansion membrane 88 outwardly against the wall W of the bore hole H, thus making removal difficult.

In operation, the probe 10 is connected to the lower end of a drill stem 12 by threading a conventional fixture 14 onto the stub 154. When lowered down a dry hole, the cavity 58 does not contain any hydraulic fluid at this time. When the probe 10 has been lowered to the proper depth, hydraulic fluid is pumped into the cavity 50 through hose 24 and port 150 while air escapes from the cavity 50 through port 152 and hose 26. The cavity 58 is pressurized to a predetermined value, and the pressurized fluid is communicated to the inside surface of the expansion membrane 88 through the slots 56. The internal pressure of the hydraulic fluid forces the membrane 88 to expand against the walls W of the bore hole H. The pressure in the cavity 58 is measured by the pressure cell 152 which supplies an electrical indication to the readout device on the surface through wires extending through one of the hoses 24, 26. As the membrane 88 expands, th feeler members 60 are forced outwardly by their respective springs 70 and the degree of radial movement of the feeler members 60 is measured by the strain gauges 72 mounted on the springs 70. The strain gauges 72 are connected to conventional bridge and amplifying circuits on the circuit board 140 which generates an electrical indication of the radial movement of the feeler members 60. The electrical indication so generated for a given pressure indication from the pressure cell 152 provides an indication of the characteristics of the material surrounding the bore hole H. The feeler members 60 contact the inside surface of the bladder 88 over a fairly large area so that localized expansions of the membrane 88 do not unduly affect the resulting measurement. The reinforcing fingers 102 provide inwardly directed forces against the expansion membrane 88 in the area 34 so that the expansion membrane 88 is capable of withstanding unusually high pressures. Regardless of the expansion of the cavity 58, the feeler members 60 are retained in the slots 56 because the retaining rings 64 limit the radial movement of the feeler members 60 by contacting the retaining tabs 62. However, the feeler members 60 will be incapable of measuring subsequent expansions of the bladder 88 as pressure is further increased. After the test has been completed air, is pumped through the hose 26 and port 152 into the cavity 58 thereby driving hydraulic fluid through conduit 158 and into the hose 24 through port 24. When all of the fluid is removed from the cvity 58, the test probe is raised from the bore hole H by lifting the drill stem 12.

It is thus seen that the inventive bore hole test probe is capable of providing accurate measurements of the characteristics of a material in which the bore hole is formed even though the material is fairly nonhomogeneous, and it is capable of making such measurements even where the material is fairly hard and thus requires relatively high pressures to expand the membrane 88.

I claim:

1. A bore hole test probe, comprising:
   a cylindrical body having a hollow core and end portions tapering inwardly to form respective reduced diameter sleeves;

a resilient, cylindrical expansion membrane having opposite ends extending along the tapered portions of said body, said body having a fluid passage extending between said core and said expansion membrane such that pressure applied to said core outwardly expands said expansion membrane;

respective annular clamping members surrounding said sleeves and having inner surfaces tapered to match the taper of said cylindrical body, said clamping members being forced toward each other to compress the ends of said expansion membrane between said clamp members and the tapered portions of said body;

a plurality of axially spaced, circumferential grooves surrounding the tapered portions of said body to maximize the bond between said expansion membrane and said body;

feeler means resiliently biased against the inside surface of said expansion membrane for providing an indication of expansion thereof; and a plurality of circumferentially spaced reinforcing fingers extending longitudinally along the outer surface of said expansion membrane at the junctions between said expansion member and said body to reinforce said expansion membrane against relatively strong shear stresses produced near said junction.

2. A bore hole test probe, comprising:

a cylindrical body having a hollow core and end portions tapering inwardly to form respective reduced diameter sleeves;

a resilient, cylindrical expansion membrane having opposite ends extending along the tapered portions of said body, said body having a fluid passage extending between said core and said expansion membrane such that pressure applied to said core outwardly expands said expansion membrane;

respective annular clamping members surrounding said sleeves and having inner surfaces tapered to match the taper of said cylindrical body, said clamping members being forced toward each other to compress the ends of said expansion membrane between said clamp members and the tapered portions of said body;

feeler means resiliently biased against the inside surface of said expansion membrane for providing an indication of expansion thereof; and a plurality of circumferentially spaced reinforcing fingers extending longitudinally along the outer surface of said expansion membrane at the junctions between said expansion member and said body to reinforce said expansion membrane against relatively strong shear stresses produced near said junction, said reinforcing fingers projecting from a collar positioned between each end of said expansion membrane and the tapered surfaces of said clamps, with the fingers at one end of said body projecting toward the fingers at the other end of said body along the surface of said expansion membrane.

3. A bore hole test probe, comprising:

a cylindrical body having a hollow core and a plurality of circumferentially spaced, longitudinally extending grooves;

a resilient, cylindrical expansion membrane surrounding said body, said expansion membrane having opposite ends extending into said body and being secured thereto, said body having a fluid passage extending between said core and said expansion membrane such that pressure applied to said core outwardly expands said expansion membrane; and an elongated bar loosely positioned in each of said grooves such that said bars can slide radially inwardly and outwardly within said grooves, said bars being resiliently biased in an outward direction such that the outer surfaces of said bars contact the inner surface of said expansion membrane, thereby providing an indication of the expansion of said expansion membrane responsive to fluid pressure applied to the core of said body, each of said bars contacting said expansion membrane along a substantial area with respect to local variations in the expansion of said expansion membrane such that the radial movement of each bar is proportional to the average expansion of said expansion membrane, said probe further including transducer means for providing an electrical indication of the radial movement of said bars whereby said electrical indication in relation to the fluid pressure applied to the core of said body provides an indication of the characteristics of the material surrounding said bore hole.

4. The bore hole test probe of claim 3, wherein a retaining tab is formed at the inside end of each bar, said probe further including a pair of annular retaining rings surrounding said body and overlying said grooves at opposite ends thereof above said retaining tabs such that said bars are retained in said grooves by said retaining tabs contacting said retaining rings.

5. A bore hole test probe, comprising:

a cylindrical body having a hollow core;

a plurality of circumferentially spaced, longitudinal grooves extending between said core and the outer surface of said body, said body having ends tapering inwardly and terminating in reduced diameter sleeves;

a generally cylindrical expansion membrane surrounding the portion of said cylindrical body containing said grooves, the ends of said expansion membrane extending along the tapered portions of said body;

an elongated bar loosely positioned in each of said grooves such that each of said bars slide radially inwardly and outwardly in its respective groove, while the outer surface of said bar remains parallel to the outer surface of said body;

bias means for resiliently biasing said bars in a radially outward direction such that the outer surfaces of said bars contact the inner surface of said expansion membrane of a substantial area in relation to localized variations in the expansion of said membrane;

transducer means for providing an electrical indication of the radial position of said bars;

a retaining collar surrounding each portion of said expansion membrane which extends along the tapered portions of said body, said reinforcing collar having a plurality of circumferentially spaced resilient fingers extending along the outer surface of said expansion membrane toward each other; and an annular clamp member having an inner surface tapered to match the taper of said body surrounding each of said sleeves, said clamp members being forcibly biased toward each other to frictionally grip said reinforcing collar and the ends of said expansion membrane between said clamp members and said body.

6. The bore hole test probe of claim 5, further including a plurality of flexible protective strips extending along the outer surface of said expansion membrane.

7. The bore hole test probe of claim 6, wherein the ends of said protective strips are positioned between respective annular collars surrounding each of said sleeves, said collars being forcibly biased toward each other to grip the ends of said protective strips therebetween.

8. The bore hole test probe of claim 5, wherein said body further includes a pair of fluid ports formed at the upper end thereof, said probe further including a tube extending downwardly from one of said fluid ports to a position beneath the lower end of the lowermost groove such that hydraulic fluid may be removed from said core by injecting air into the other of said fluid ports.

9. A bore hole test probe, comprising:
a cylindrical body having a hollow core;
a resilient, cylindrical expansion membrane surrounding said body, said expansion member having opposite ends extending into said body and being secured thereto, said body having a fluid passage extending between said core and said expansion membrane such that pressure applied to said core outwardly expands said expansion membrane;
feeler means resiliently biased against the inside surface of said expansion membrane for providing an indication of expansion thereof; and
a plurality of reinforcing fingers extending longitudinally along the outer surface of said expansion membrane at the junctions between said expansion member and said body, said reinforcing fingers being formed by generally elongated plates closely spaced from each other to provide substantially continuous reinforcement for said expansion membrane against relatively strong shear stresses produced near said junction.

10. A bore hole test probe, comprising:
a cylindrical body having a hollow core and a plurality of circumferentially spaced, longitudinally extending grooves;
a resilient, cylindrical expansion membrane surrounding said body, said expansion membrane having opposite ends secured to said body, said body having a fluid passage extending between said core and said expansion membrane such that pressure applied to said core outwardly expands said expansion membrane;
an elongated feeler member positioned in each of said grooves such that said feeler members can slide radially inwardly and outwardly within said grooves, each of said feeler members being resiliently biased in an outward direction against the inner surface of said expansion membrane at a point between the ends of said feeler members, with said feeler members being free to pivot about said point to conform to the surface of said expansion membrane; and
transducer means for providing an electrical indication of the radial movement of said feeler members whereby said electrical indication in relation to the fluid pressure applied to the core of said body provides an indication of the characteristics of the material surrounding said bore hole.

11. The bore hole test probe of claim 10, wherein a retaining tab is formed at the inside end of each feeler member, said probe further including a pair of annular retaining rings surrounding said body and overlying said grooves at opposite ends thereof above said retaining tabs such that said feeler members are retained in said grooves by said retaining tabs contacting said retaining rings.

* * * * *